United States Patent
Da Silva Rodrigues et al.

(10) Patent No.: US 9,784,850 B2
(45) Date of Patent: Oct. 10, 2017

(54) MULTIMODAL IMAGING APPARATUS

(71) Applicant: KONINKLIJKE PHILIPS N.V., Eindhoven (NL)

(72) Inventors: Pedro Jorge Da Silva Rodrigues, Veldhoven (NL); Andreia Maria Araujo Trindade Rodrigues, Veldhoven (NL); Herfried Karl Wieczorek, Aachen (DE); Gereon Vogtmeier, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/917,030

(22) PCT Filed: Sep. 18, 2014

(86) PCT No.: PCT/EP2014/069862
§ 371 (c)(1),
(2) Date: Mar. 7, 2016

(87) PCT Pub. No.: WO2015/044019
PCT Pub. Date: Apr. 2, 2015

(65) Prior Publication Data
US 2016/0209515 A1    Jul. 21, 2016

(30) Foreign Application Priority Data
Sep. 27, 2013  (EP) ..................................... 13186325

(51) Int. Cl.
*G01T 1/16*       (2006.01)
*G01T 1/29*       (2006.01)
(Continued)

(52) U.S. Cl.
CPC ............ *G01T 1/1603* (2013.01); *A61B 6/037* (2013.01); *A61B 6/4417* (2013.01); *G01T 1/2985* (2013.01)

(58) Field of Classification Search
CPC ..................................................... G01T 1/1603
See application file for complete search history.

(56) References Cited

U.S. PATENT DOCUMENTS 5,591,977 A * 1/1997 Green ................... G01T 1/2985
250/363.03
5,608,221 A     3/1997 Bertelsen
(Continued)

FOREIGN PATENT DOCUMENTS

| WO | 02/079802    | 10/2002 |
|----|--------------|---------|
| WO | 2010/136851  | 12/2010 |
| WO | 2012/066469  | 5/2012  |

OTHER PUBLICATIONS

Hongdi Li, et al., "The Engineering and Initial Results of a Transformable Low-cost High-resolution PET Camera", IEEE Transactions of Nuclear Sciene, vol. 54, No. 5, Oct. 1, 2007.

*Primary Examiner* — David Porta
*Assistant Examiner* — Hugh H Maupin

(57) ABSTRACT

A multimodal imaging apparatus (1*a*, 1*b*) including scintillator elements (31) for capturing incident gamma quanta (25, 61) and for emitting scintillation photons (26) in response to said captured gamma quanta (25, 61). Photosensitive elements (33) capture the emitted scintillation photons (26) and determine a spatial distribution of the scintillation photons. The imaging apparatus (1*a*, 1*b*) is configured to be switched between a first operation mode for detecting low energy gamma quanta and a second operation mode for detecting high energy gamma quanta. The scintillator elements are arranged to capture incident gamma quanta (25, 61) from the same area of interest (65) in both
(Continued)

operation modes. The scintillator elements (31) include a first region with high energy scintillator elements (27) for capturing high energy gamma quanta and a second region with low energy scintillator elements (29) for capturing low energy gamma quanta. A positioning mechanism (35) changes the orientation of the scintillator elements (31), in particular for tilting the scintillator elements (31), to switch between operation modes.

18 Claims, 9 Drawing Sheets

(51) Int. Cl.
*A61B 6/03* (2006.01)
*A61B 6/00* (2006.01)

(56) References Cited

U.S. PATENT DOCUMENTS

| | | |
|---|---|---|
| 5,841,140 A | 11/1998 | McCroskey |
| 6,303,935 B1 | 10/2001 | Engdahl |
| 6,362,479 B1 | 3/2002 | Andreaco |
| 6,448,559 B1 | 9/2002 | Saoudi |
| 6,534,771 B1 | 3/2003 | Rozsa |
| 7,138,635 B2 | 11/2006 | Heismann |
| 7,262,415 B2 | 8/2007 | Crosetto |
| 2004/0159791 A1 | 8/2004 | Hefetz |
| 2004/0251419 A1 | 12/2004 | Nelson |
| 2007/0205367 A1 | 9/2007 | Deman |
| 2008/0111081 A1 | 5/2008 | Chuang |
| 2012/0136237 A1 | 5/2012 | Baviera |
| 2012/0265050 A1 | 10/2012 | Wang |
| 2015/0335301 A1* | 11/2015 | Hermony ............... A61B 6/032 250/370.08 |

* cited by examiner

MULTIMODAL IMAGING APPARATUS

CROSS REFERENCE TO RELATED APPLICATIONS

This application is the U.S. National Phase application under 35 U.S.C. §371 of International Application No. PCT/EP2014/069862, filed Sep. 18, 2014, published as WO 2015/044019 on Apr. 2, 2015, which claims the benefit of European Patent Application Number 13186325.0 filed Sep. 27, 2013. These applications are hereby incorporated by reference herein.

FIELD OF THE INVENTION

The present invention relates to a multimodal imaging apparatus for imaging a radiotracer distribution within a subject.

BACKGROUND OF THE INVENTION

Single Photon Emission Computed Tomography (SPECT) and Positron Emission Tomography (PET) are, either self-contained or in combination with Computed Tomography (CT) or Magnetic Resonance Imaging (MRI), two common techniques for imaging the human body or parts thereof. In particular, PET and SPECT allow imaging organs or metabolic processes in the human body and, e.g., determine therefrom the progress of a disease. For this, a patient is usually administered a radioactive tracer substance emitting particles, i.e. radiation, that can be captured and used as a basis for imaging. Further applications include preclinical studies, wherein small animals are imaged in order to determine the effects of new medication or treatment approaches. Also other imaging applications outside the field of medicine exist relying on the same principles.

For some applications, in particular medical applications, it can be advantageous to provide both, SPECT and PET, images of the same area of interest in a patient in order to exploit the advantages of both imaging modalities. Although making use of the same basic imaging approach (detecting gamma rays), the two most common imaging systems SPECT/CT and PET/CT, are currently, however, usually offered in different mechanical, frontend electronics and backend processing configurations. This leads to a more complicated supply chain for the different imaging systems and difficulties in the upgradability. Usually, PET and SPECT systems require different mechanical structures, different data acquisition paths and different photodetectors or combinations of photodetectors leading to little possible savings when combining the two imaging modalities in order to obtain a multimodal imaging device for providing images based on both imaging modalities.

In Mediso, "AnyScan: Triple Modality Molecular Imaging System", product brochure, October 2011, there is introduced the AnyScan hybrid imaging system for early diagnosis and treatment for cancer, cardiac and neurological diseases. The presented device allows obtaining SPECT and PET images of a patient by means of a combined imaging system. The presented system comprises two separate imaging modalities, wherein each of the separate imaging modalities uses a separate gantry and separate electronics processors. The two devices can be mechanically coupled for obtaining PET and SPECT images of a patient.

One disadvantage of this solution, however, is that it requires two separate gantries, i.e. a rather complex and costly mechanical construction, and basically comprises two separate imaging devices placed side by side. Further, in order to obtain PET and SPECT images of one specific area of interest the patient has to be moved versus the two gantries because each of the two devices focuses a separate area of interest, which may lead to further difficulties if exact positioning or combination of the PET and SPECT information is required.

In U.S. Pat. No. 6,448,559 B1 a detector assembly for multi-modality scanners is disclosed. The assembly comprises a first layer for detecting low energy gamma radiation and X-rays and a second layer for detecting high energy gamma radiation. The first layer is generally transparent to high energy gamma radiation. The second layer may advantageously provide measurement of depth of interaction of the high energy radiation. The detector assembly is advantageously incorporated in a multi-modality PET/SPECT/CT scanner allowing simultaneous transmission and emission imaging with the same detection geometry.

In WO 02/079802 A2, systems and methods are described for a positron emission tomography camera with individually rotatable detector modules and/or individually movable detector modules. Further, a plurality of individually moveable shield sections are disclosed.

In US U.S. 2008/111081 A1 an imaging system and method for the non-pure Positron Emission Tomography are presented. The systen comprises a PET subsystem to detect the annihilated photons and a SPECT subsystem to detect the associated gamma. These two subsystems are connected by a triple coincidence circuit.

SUMMARY OF THE INVENTION

It is thus an object of the present invention to provide an improved multimodal imaging apparatus for imaging a radiotracer distribution within a subject, which overcomes the disadvantages of current multimodal imaging devices. It is further an object to provide the possibility to obtain images based on emitted radiation (in particular gamma radiation or gamma quanta) in a wider energy range and to avoid making use of two separate imaging systems leading to a complex mechanical construction and higher costs.

In an aspect of the present invention there is presented a multimodal imaging apparatus for imaging a radiotracer distribution within a subject, said process causing the emission of gamma quanta, said apparatus comprising a scintillator including scintillator elements for capturing incident gamma quanta generated by the radiotracer and for emitting scintillation photons in response to said captured gamma quanta, a photodetector including photosensitive elements for capturing the emitted scintillation photons and for determining a spatial distribution of the scintillation photons, and a readout electronics for determining the impact position of an incident gamma quantum in the scintillator and/or a parameter indicative of the emission point of the gamma quantum in the subject based on the spatial distribution of the scintillation photons, wherein the imaging apparatus is configured to be switched between a first operation mode for detecting low energy gamma quanta and a second operation mode for detecting high energy gamma quanta, wherein the high energy gamma quanta have a higher energy than the low energy gamma quanta, and the scintillator is arranged to capture incident gamma quanta from the same area of interest in the first operation mode and in the second operation mode without requiring a relative movement of the subject versus the scintillator; wherein the scintillator comprises an array of scintillator elements including a first region with high energy scintillator elements for capturing high energy gamma quanta and a second region with low energy scintillator elements for capturing low energy gamma quanta; and/or the apparatus further comprises a positioning mechanism for changing the orientation and/or position of the scintillator elements, in particular for tilting the scintillator elements, to switch the imaging apparatus between the first operation mode and the second operation mode.

The presented multimodal imaging apparatus allows imaging processes causing the emission of gamma quanta, i.e. gamma rays or high energy photons, sometimes also referred to as gamma particles and, thus, imaging a radiotracer distribution within a subject. These gamma quanta may be emitted indirectly by a positron-emitting radionuclide (such as for PET imaging) or by a radionuclide directly emitting photons (such as for SPECT imaging). Such a radionuclide (also referred to as radiotracer) may, e.g., be administered to a patient in form of a tracer substance. This tracer substance usually also comprises other elements and may form chemical compounds which interact with the metabolism process in a patient. Then, the location of the tracer substance or the concentration in a specific organ may be imaged by evaluating the gamma quanta emitted by the tracer.

The imaging apparatus according to the present invention may also integrate a CT or MRI imaging system that allows (simultaneously) imaging anatomic information of the subject. Then, anatomic images can be combined with the acquired images of the process in the subject in order to provide meaningful information to a physician.

The emitted gamma quanta are captured by means of a scintillator, which comprises a scintillating material, i.e. a material that emits scintillation photons in response to captured gamma quanta. Coupled to this scintillator there is provided a photodetector, in particular a scintillation photon counting photodetector, which allows capturing the emitted scintillation photons and determine therefrom a spatial distribution of the scintillation photons, for instance in the form of a charge-distribution. Thereby a charge-distribution basically corresponds to a representation of the spatial distribution of the scintillation photons on a two-dimensional array of photosensitive elements. Photosensitive elements herein particularly refer to different types of photodiodes such as digital or analog silicon photomultipliers (SiPM). According to the present invention, the photodetector is preferably capable of implementing a scintillation photon counting approach with a high dynamic range allowing the detection of scintillation photons of different energies. In particular, the photodetector has a dynamic range that allows it to be coupled to different types of scintillators and provide a light yield output compatible with both SPECT and PET imaging.

The spatial distribution of the scintillation photons is read out by a readout electronics, which, on the one hand, allows determining the impact position of the incident gamma quantum that caused the emission of the scintillation photons in the apparatus and/or, on the other hand, a parameter indicative of the original emission point of the gamma quantum, in the subject. Based on a plurality of impact positions in the scintillator and/or emission points of the gamma ray in the subject, it is possible to generate images representing the accumulation of the tracer substance and in particular the regions with higher or lower amount of tracer substance deposition or metabolization. The generated images may thereby include image sequences, i.e. moving images or videos, as well as fixed-images. According to the present invention the imaging apparatus may be switched between a first operation mode which allows detecting low energy gamma quanta and a second operation mode which allows detecting high energy gamma quanta.

It is thereby particularly advantageous that only one readout electronics, i.e. a common data acquisition, is used for detecting low energy gamma quanta and high energy gamma quanta. Low energy gamma quanta thereby particularly refer to gamma rays with an energy of around 70-250 keV as, e.g., emitted in a SPECT imaging procedure using thallium-201, technetium-99m, iodine-123, or indium-111 radio isotopes. High energy gamma quanta may thereby particularly refer to 511 keV gamma photons emitted after an electron-positron decay of a radioactive substance such as fluorodeoxyglucose labeled with fluorine-18 (FDG) as used in clinical PET scanning. Further, the present invention allows capturing low energy gamma quanta and high energy gamma quanta without requiring the patient to be moved relative to the scintillator. Thus, the patient may remain at the same position while multimodal images are generated. For instance, PET and SPECT images from substantially the same area of interest may be generated without requiring to move the patient.

The proposed apparatus may further use a common electronics architecture that can support different photon counting detectors, with different requirements of power current and voltages while being compatible with a single mechanical structure.

In a preferred embodiment of the multimodal imaging apparatus according to the present invention the energy of both the low energy gamma quanta and the high energy gamma quanta lies between 70 keV and 600 keV (or by a combination of radionuclides combined in one or multiple pharmaceutical compounds administrated to a patient simultaneously or in a phased approach). One advantage of the present invention is that not only gamma quanta in a small energy range can be captured but that a higher range is possible. Thereby, the imaging apparatus according to the present invention may allow, e.g., the simultaneous or sequential generation of SPECT and PET images of the same area of interest in a subject.

In another embodiment the multimodal imaging apparatus further comprises a common gantry for supporting the scintillator and the photodetector in the first operation mode and in the second operation mode. In contrast to previous solutions or systems, which usually make use of two separate gantries and two separate readout electronics for generating images of a process in a subject causing the emission of low energy gamma quanta (as in SPECT imaging) on the one hand and the emission of high energy gamma quanta (as in PET imaging) on the other, the present invention allows saving costs by using a single, i.e. common, gantry. It is further possible to reduce the amount of electronics, e.g. by using one processor (readout electronics) for processing the signals for both low energy and high energy signals instead of two separate processors according to further embodiments of the present invention. By making use of a common gantry the present invention allows imaging the same area of interest (in a subject) without requiring moving the subject versus the gantry. This allows efficiently using two different imaging modalities for providing images of a single area of interest in a subject and has the advantage that the subject does not need to be moved. Moving the subject could have an influence on the process or the organ being imaged and may make it difficult to obtain PET and SPECT images from the very same (spatiotemporal) area of interest.

According to another embodiment of the present invention the multimodal imaging apparatus further comprises a collimator for filtering the incident gamma quanta based on the angle of incident in the first operation mode. Such a collimator usually refers to a device for narrowing a beam of gamma quanta (or other particles) and may, e.g. comprise a block of a non-transparent shielding material such as lead, molybdenum, tungsten or depleted uranium including a plurality of appropriately aligned boreholes. Also an arrangement of folded sheets of such non-transparent materials may be comprised in the collimator. Narrowing herein means to align the directions of motions of the different gamma quanta. The main effect of the collimator is the selection of quanta that are emitted from the radioisotope under certain angles. Thereby imaging by use of parallel holes or a pinhole is enabled, similar to the use of a lens or a pinhole in optical imaging. Another advantage of making use of collimator in the present invention is that it allows filtering out gamma quanta, in particular gamma rays, that are not travelling in the desired direction, i.e. that do not originate from the area of interest. The angle of incidence under which incident gamma quanta can pass the collimator is thereby in particular specified as the direction of the subject to be examined. The resulting image is only based on the desired gamma quanta, i.e. the gamma quanta that are not filtered out. The collimator may thereby also be adjustable, i.e. variable in its filtering angle. SPECT imaging, e.g., usually requires the use of a collimator as single photons are detected and the imaging is based on all captured gamma quanta. Thus, if gamma quanta originating from other sources than the process in the subject to be imaged were also captured, the generated image would not be meaningful with respect to the process in the subject representing the originally desired purpose of the imaging but would show a range of side effect obscuring the intended image. In PET imaging, in contrast thereto, usually no collimator is required because the incident gamma quanta are filtered based on a coincidence detection in which only incident gamma quanta are considered in the imaging that have a coincident event on the opposite side of the subject.

In another embodiment the scintillator elements include high energy scintillator elements for capturing high energy gamma quanta and low energy scintillator elements for capturing low energy gamma quanta and/or the photodetector is configured for operation in photon counting mode, wherein the dynamic range of the photodetector is configured to capture scintillation photons emitted by both the high energy scintillator elements and by the low energy scintillator elements. Usually scintillators and in particular scintillator arrays comprise one single type of scintillator elements only. Depending on the material and the dimensions of these scintillator elements their reaction in response to incident gamma quanta varies significantly. If, e.g. the scintillator elements comprise organic crystals or liquids the reaction, i.e. the amount emitted scintillation photons in response to incident gamma quanta, may be particularly suited for the detection of heavy ions. According to the present invention, preferably inorganic scintillators such as high-Z inorganic crystals like LYSO or BGO, YAG:Ce, ceramic garnets based on the formula $(M1,M2)_3(M3,M4)_5O_{12}$:Ce with M1 and M2 elements of the group (Sc, Y, rare earth metals, Mg, Ca) and M3 and M4 of the group (Al, Ga, In, Sc, Lu, Mg, Ca) or others are used in the scintillator. For these inorganic crystals one main criterion is their thickness (i.e. their length). Usually a thicker scintillator crystal is better suited for the detection of high energy gamma rays than a thinner scintillator crystal. One main advantage of combining different scintillator elements in one scintillator array is that both high energy gamma quanta and low energy gamma quanta may be captured without needing to use two different scintillator crystal arrays. Both kinds of gamma quanta can be captured and used as the basis for imaging. Making use of different types of scintillator elements within one scintillator array allows reading out only a subset of the scintillator elements depending on the operation mode of the imaging apparatus.

The use of ceramic garnets with the basic formula $(M1,M2)_3(M3,M4)_5O_{12}$:Ce as indicated above has the advantage that an inexpensive material (in comparison to single crystals like LYSO) can be used, which shows preferred properties for both operation modes. On the one hand it shows time-of-flight performance for high energy imaging (high energy gamma quanta as, e.g., used in PET imaging). On the other hand it shows high light output, up to two times the value of LYSO, which is advantageous for low energy imaging (low energy gamma quanta as, e.g. used in SPECT imaging). In addition, such ceramic garnets, e.g. $(Lu,Gd)_3(Ga,Al)_5O_{12}$:Ce, have typically one fourth of the lutetium amount per volume, compared to LYSO. The intrinsic radioactivity is therefore strongly reduced, resulting in a lower background level and therefore better signal-to-noise performance of the detector in both operation modes.

Further, the photodetector is configured for operation in photon counting mode and to provide a high enough dynamic range for capturing scintillation photons emitted by the high energy scintillator elements and by the low energy scintillator elements. High enough means that the photodetector is capable of counting the number of detected optical photons, either in a linear or saturated scale up to the high energy photons (511 keV). The end point of the dynamic range should be high enough to account for different scintillators (which have different light yield). Different scintillators will produce different number of optical photons for the high energy photons (511 keV). Advantages offered by a photon counting photodetector (e.g. like the Philips DPC) are typical a single photon resolution, better timing, lower bias voltage (e.g. 25-65 V) and very high gain (e.g. 106). The other solid state sensors (like APDs) are typically fully analog, poor timing and require higher bias voltage making integration mode demanding. For example the required dynamic range of the photodetector for high and low energy scintillators may be covered with two versions of the PDPC sensor. One version can count between 1 and around 6400 photons, the other version can count between 1 and 3200 photons. Both are suitable for the current generation of scintillator, from the low light yield BGO up to the high regime of ceramic garnets. Both have been used to readout SPECT and PET scintillators. It may, however, also be possible to put a further refinement from 1 to 122800 photons, which could be used for even brighter scintillator like LuI:Ce for example, which has almost 100000 optical photons per MeV (almost a factor 10× higher than BGO).

According to another embodiment the imaging apparatus further comprises a positioning mechanism for changing the orientation and/or position of the scintillator elements, in particular for tilting the scintillator elements, to switch the imaging apparatus between the first operation mode and the second operation mode. Tilting herein refers to physically rotating the scintillator elements. If, e.g., the scintillator elements are designed in the form of cuboids with different edge lengths it becomes possible to direct different sides of the cuboid in the direction of the process causing the emission of gamma quanta to be captured by rotating this cuboid. Depending on how the scintillator element is tilted, i.e. oriented, the thickness or the depth of the crystal, i.e. the length incident gamma quanta may travel through the scintillator element (crystal) and thereby cause the emission or scintillation photons varies. Usually, the higher the energies of the incident gamma quanta, the thicker the crystals are needed in order to absorb an adequate number of gamma quanta for allowing the generation of an image representing the process in a subject. Usually PET scintillators comprise thicker scintillator elements than SPECT scintillators. The positioning mechanism according to the present invention thereby preferably allows a 90° rotation of the scintillator elements. In the first operation mode the first side of a scintillator element (single scintillator crystal) is oriented versus the subject and in the second operation mode an orthogonal surface of the scintillator element is oriented versus the subject.

Depending on the orientation, the scintillator elements are either exposed to the incident gamma quanta with their first or second side leading to a different thickness in the direction of the incident gamma quanta. Alternatively to rotating, the positioning mechanism may also be designed in the form of a shifting or movement mechanism that allows shifting or moving the scintillator elements from one position to another, e.g. along a guide rail structure or the like, and thereby switch turn between a first and second operation mode.

According to yet another embodiment of the multi-model imaging apparatus a photosensitive element is coupled to a scintillator element and arranged to capture the scintillation photons emitted by said scintillator element and the positioning mechanism is configured to change the orientation and/or position of the scintillator elements (31) and the thereto coupled photosensitive elements, in particular to tilt the scintillator elements and the thereto coupled photosensitive elements, for switching the imaging apparatus between the first operation mode and the second operation mode. By making use of one-to-one coupling wherein each scintillator element is coupled to a dedicated photosensitive element and read out separately, a more flexible design of the positioning mechanism becomes possible. If, e.g. the scintillator elements are cuboid-formed with a photosensitive element coupled to one side of the cuboid, it becomes possible to tilt, i.e. rotate, the scintillator elements and the thereto coupled photosensitive elements in the direction of the subject to be imaged either with the cuboid side opposite of the photosensitive elements, or with one of the cuboid sides orthogonal to the photosensitive element. The detection of scintillation photons is possible independent of the side of the scintillator element to which the photodetector element is attached. One advantage of this embodiment is that the depth of the scintillator element, i.e. the distance a gamma quantum originating from the process in the subject can travel through the crystal, can be varied. This avoids the depth-of-interaction effect in PET imaging. According to this embodiment, the scintillator elements are again preferably rotated by 90° for switching between the two operation modes.

According to yet another embodiment a photosensitive element is coupled to a scintillator element and arranged to capture the scintillation photons emitted by said scintillator element, a subset of the scintillator elements and the thereto coupled photosensitive elements is mechanically coupled to form a detection assembly and the positioning mechanism is configured to change the orientation and/or position of the detection assembly, in particular to tilt the detection assembly, for switching the imaging apparatus between the first operation mode and the second operation mode. Similar to the above-described principle of rotating the scintillator elements it is also possible to tilt, i.e. to rotate, a detection assembly comprising multiple scintillator elements and photosensitive elements coupled thereto. One advantage of tilting a detection assembly instead of tilting single scintillator elements is that the positioning mechanism may be simpler. A detection assembly may thereby, e.g., comprise 4 scintillator elements. Multiple detection assemblies comprising scintillator elements and photosensitive elements may be tilted separately in order to switch between the first operation mode and the second operation mode.

In yet another embodiment a detection assembly includes a stack of scintillator elements and the positioning mechanism is configured to tilt said stack of scintillator elements for switching the imaging apparatus between a first position corresponding to the first operation mode in which the incident gamma quanta impact on the side face of the stack and a second position corresponding to the second operation mode in which the incident gamma quanta impact on the top face of the stack. Preferably the single scintillator elements are stacked, i.e. arranged in a stack structure to form a detection assembly. It is thereby either possible to read out each scintillator element separately (one-to-one coupling) or to make use of light-sharing (detecting the scintillation photons generated by a single scintillator element with multiple photosensitive elements). Such a stack structure may be tilted in the direction of the subject to be imaged with its side face, i.e. with multiple scintillator elements aligned next to one another to detect gamma quanta emitted by the process in the subject to be imaged. Alternatively the stack may also be tilted with the top face of the stack pointing in the direction of the subject, such that only one scintillator element may directly capture gamma quanta emitted by the process in the subject but these gamma quanta may travel through the different scintillator elements one after another and thereby generate a plurality of scintillation photons. By tilting the top face of the stack in the direction of the process in the subject it becomes thus possible to provide a thicker (i.e. longer) scintillator element, i.e. multiple scintillator elements arranged in a stack one behind another, such that gamma quanta can travel from one scintillator element to the next, and thereby particularly detect high energy gamma quanta in order to present a longer absorption depth to received gamma quanta. There may be comprised an optical coupling between the scintillator elements such as light-conducting glue.

In another embodiment of the present invention the scintillator comprises a first array of high energy scintillator elements and a second array of low energy scintillator elements and the second array is arranged between the first array and the subject and coupled to the first array by means of an optical coupling layer. Thus, the gamma quanta emitted by the process in the subject initially impact on the second array and may pass through that second array if their energy is high enough. The optical coupling layer herein particularly comprises light-conducting glue. This optical coupling layer allows guiding the scintillation photons emitted in the second array, i.e. the array of low energy scintillator elements, into the first array. Preferably, all scintillation photons are captured by a photodetector coupled to the first array. Thus, scintillation photons generated in the second array as well as scintillation photons generated in the first array may be captured with the same photodetector. This photodetector is usually coupled to the first array. High energy gamma quanta impact on the second array but usually pass through the second array as this second array is usually not able to stop the high energy gamma quanta. Thus, such high energy gamma quanta are mainly captured in the first array only and cause the emission of scintillation photons therein. One advantage of this embodiment is that both high energy gamma quanta as well as low energy gamma quanta may be detected simultaneously. The scintillator elements in the first array (high energy scintillator elements) may particularly be represented by ceramic garnet scintillator elements optimized for high stopping power and short decay time. Such scintillator elements are usually used for PET and PET time-of-flight imaging. The scintillator elements in the second array (low energy scintillator elements) may particularly be represented by ceramic garnet scintillator elements optimized for low background, high light yield and energy resolution. Such scintillator elements are usually used in SPECT imaging.

According to another embodiment of the present invention the scintillator comprises an array of scintillator elements including a first region with high energy scintillator elements and a second region with low energy scintillator elements. This embodiment also allows the simultaneous detection of high energy gamma quanta and low energy gamma quanta in the different regions of the scintillator elements in the scintillator array. One advantage of this embodiment is that only a single scintillator array is required. Again, the detection of high energy gamma quanta as well as the detection of low energy gamma quanta is possible.

In yet another embodiment a collimator for filtering the incident gamma quanta based on their angle of incidence is arranged between the region with low energy scintillator elements and the subject. The collimator as described above only covers a part of the scintillator array, i.e. the region comprising the low energy scintillator elements. Thus, according to this embodiment, the low energy gamma quanta are filtered such that only low energy gamma quanta emitted by the process in the subject to be imaged are captured. In contrast thereto in the region with high energy scintillator elements also gamma quanta impacting under other angles, i.e. not necessarily originating in the process in the subject to be imaged, are captured. This may, e.g., be compensated by making use of another filtering approach, such as the detection of coincidently impacting photons at two opposite sides of the subject to be imaged as, e.g., used in PET.

According to yet another embodiment of the present invention the readout electronics is configured to read out the low energy scintillator elements in the first operation mode and to read out the energy scintillator elements in the second operation mode. Thus, only a subset of the scintillator elements is read out depending on the current operation mode. This again allows the target-oriented detection of the desired gamma quanta only. Depending on the desired imaging modality, one detector module, i.e. a combination of scintillator elements, photosensitive elements and (at least part of the) readout electronics, can be configured to only detect either low energy gamma quanta or high energy gamma quanta.

According to yet another embodiment of the multimodal imaging apparatus the collimator is supported by shifting means for shifting the collimator in a first position in the direct path between the scintillator and subject or in a second position outside of the direct path between the scintillator and the subject. Such shifting means can, e.g. be incorporated by means of guiding rails which allow guiding the collimator in a first position in which it is between the scintillator and the subject to be imaged or to a second position in which it is not within this direct path. One advantage of making use of such a flexible use of a collimator being only inserted in the direct path if required, is that the detector can be optimized for detecting low energy gamma quanta in a first operation mode or high energy gamma quanta in a second operation mode, wherein the two modes require different filtering approaches. As outlined above, it may, e.g., be possible to filter the incident gamma quanta based on a collimator when detecting low energy gamma quanta, or based on coincidence detection when detecting high energy gamma quanta. This may, e.g. be advantageous when using a scintillator comprising low energy scintillator elements as well as high energy scintillator elements and being configured to allow SPECT examinations as well as PET examinations, wherein either gamma rays of energy of around 140 keV (e.g. low energy gamma quanta as used in SPECT) or gamma rays of energy around of 511 keV (e.g. high energy gamma quanta as used in PET) are to be captured.

According to yet another embodiment of the multimodal imaging apparatus according to the present invention the apparatus is configured to be switched between the first operation mode and the second operation mode by shifting the collimator from the first position to the second position. Thus, if the collimator is inserted in the direct path the apparatus is configured to the first operation mode. This flexible collimator allows configuring the apparatus for the detection of low energy gamma quanta or high energy gamma quanta.

One main advantage of the different presented embodiments of the present invention is that multimodal imaging becomes possible, in particular PET and SPECT imaging, by means of the same apparatus with a common gantry and (at least partly) shared readout electronic. Thereby costs may be reduced in comparison to devices dedicated to one imaging modality only, floor space in the hospitals may be saved and the imaging may be improved. The imaging may be further improved by making it possible to provide images of substantially the same area of interest at substantially the same time with different imaging modalities, in particular without needing to move, i.e. to relocate, a patient.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
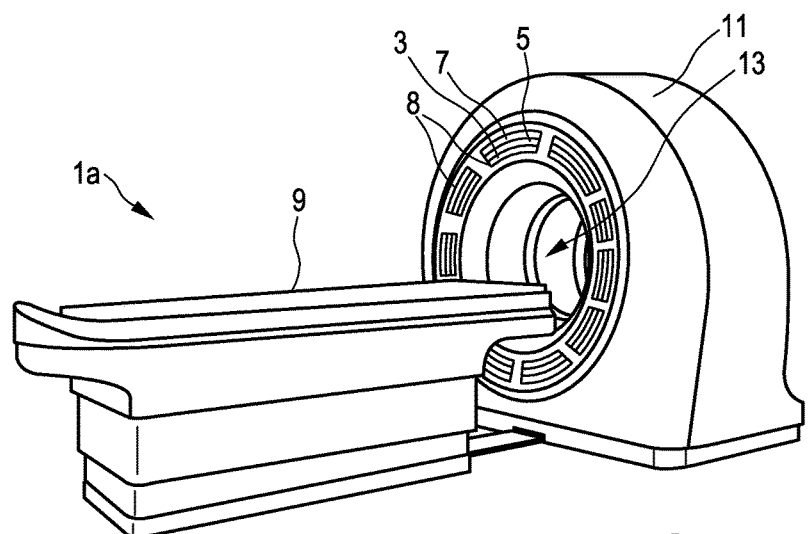
FIG. 1 shows a first embodiment of a multimodal imaging apparatus for imaging a process in a subject according to the present invention.

In FIG. 1 there is illustrated a first embodiment of a multimodal imaging apparatus 1a according to the present invention. The apparatus 1a comprises a scintillator 3 for capturing incident gamma quanta generated by a radiotracer and for emitting scintillation photons in response to captured gamma quanta and a photodetector 5 for capturing the emitted scintillation photons and for determining a spatial distribution of the scintillation photons (e.g. a charge distribution). The apparatus further comprises a readout electronics 7 for determining the impact position of an incident gamma quantum in the scintillator 3 based on the spatial distribution of the scintillation photons. A combination of scintillator 3, photodetector 5, and at least part of the readout electronics 7 may also be referred to as detection module 8. As illustrated in FIG. 1 the multimodal imaging apparatus 1a comprises multiple detection modules 8 attached to a common gantry 11. The number of detection modules 8 may vary depending on the intended application and/or imaging modality. Other parts of the readout electronics 7 may also be incorporated in a central processing unit for image reconstruction included in the apparatus. The gamma quanta usually originate from a patient (subject) on a subject support 9 that has been administered a radioactive tracer substance. The energy of the emitted radiation (high energy or low energy gamma quanta) mainly depends on the administered tracer substance.

Figure 2:
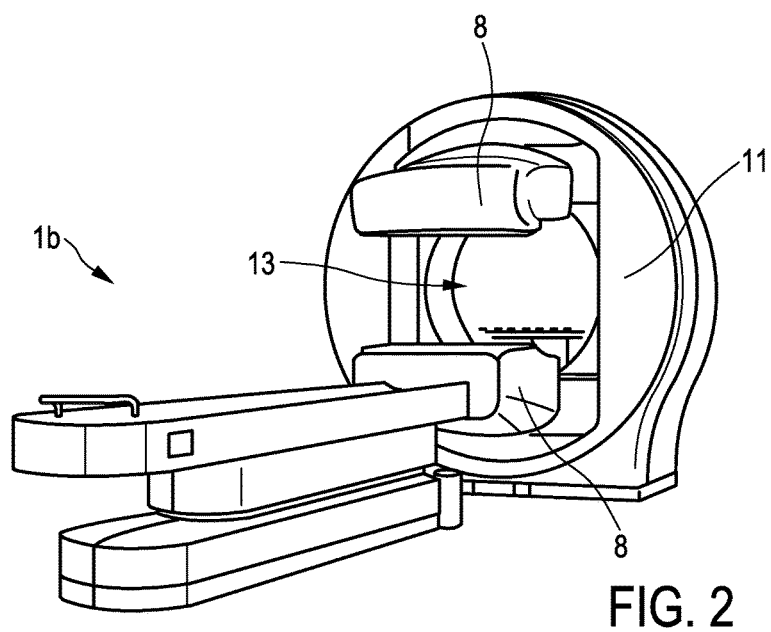
FIG. 2 shows another embodiment of a multimodal imaging apparatus according to the present invention.

Another embodiment of a multimodal imaging apparatus 1b according to the present invention is illustrated in FIG. 2. Therein, only two detection modules 8 are used and the gantry 11 is configured to be rotated around the examination area 13.

The multimodal imaging apparatus according to the present invention may particularly be used for providing both SPECT imaging (first operation mode, low energy gamma quanta, in particular with energies in the range of about 70-250 keV) as well as PET imaging (second operation mode, high energy gamma quanta, in particular with energies in the range of about 400 to 600 keV) of a subject in the examination area 13. PET imaging usually requires at least two but usually multiple detection modules 8 on two opposite sides of the examination region 13 in order to perform a coincidence filtering, i.e. filtering out gamma quanta that do not result from a process in the subject. In contrast thereto, SPECT imaging only requires one detection module 8 on one side of the subject because single photons are captured and the filtering is usually performed based on a collimator.

Figure 3:
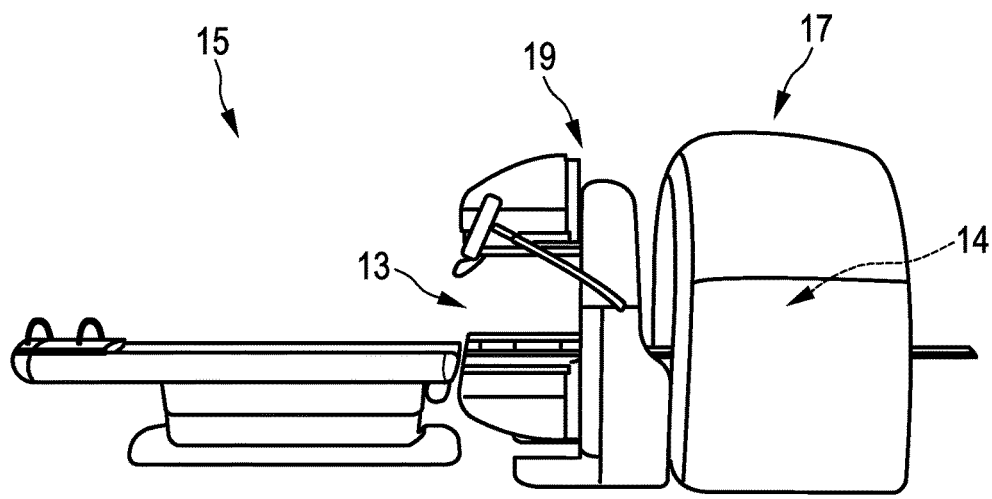
FIG. 3 shows a schematic illustration of a state of the art imaging device comprising a SPECT and a PET gantry.

Current systems for providing both PET and SPECT imaging are usually composed systems that make it necessary to move the subject relative to the imaging device in order to provide PET and SPECT images. FIG. 3 illustrates such a state of the art imaging system 15 comprising two separate gantries for providing PET images 17 and SPECT images 19. This system thus comprises two different examination areas 13, 14 for the two imaging modalities. In contrast thereto, the present invention (FIGS. 1, 2) can be switched between a first operation mode for detecting low energy gamma quanta (SPECT imaging) and a second operation mode for detecting high energy gamma quanta (PET imaging) while the subject, i.e. the patient, may remain at the same position. Advantageously, a combined (multimodal) imaging as disclosed herein allows reducing the costs of the apparatus by sharing common features such as the gantry, power supplies, common frontend and system electronics (i.e. part of the readout electronics), the cooling system or other optical or mechanical components. Costs may further be reduced by reducing the amount of the required high density scintillator material. Still further, the required floor space in a hospital can be reduced by making use of one apparatus only.

Figure 4:
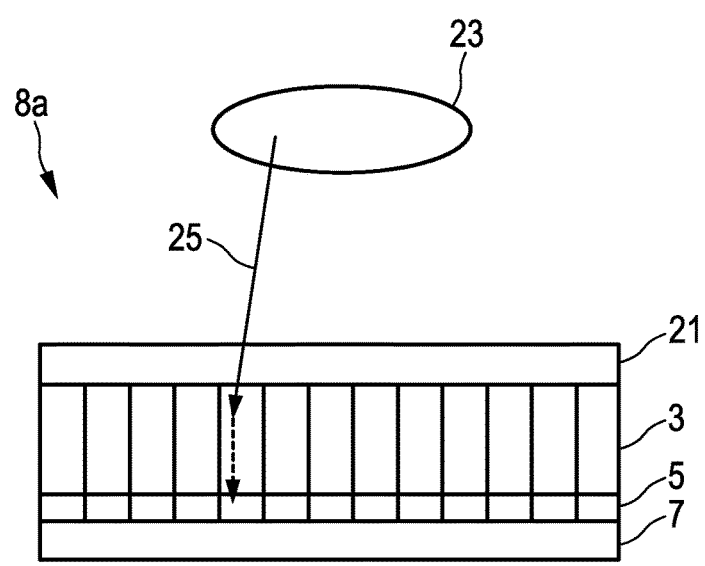
FIG. 4 shows a schematic sectional view of a state of the art detector module comprising a scintillator, a photodetector and readout electronics.

FIG. 4 further clarifies the terminology of a state of the art detector module 8a as used in a SPECT system. There is illustrated a sectional view of the detector module 8a comprising a scintillator 3, a photodetector 5, a readout electronics 7 and a collimator 21. A process in a subject 23 causes the emission of gamma quanta 25 (low energy gamma quanta in this example), which are captured by the scintillator 3. A gamma quantum 25 causes the emission of scintillation photons 26, which are then captured by the photodetector 5. Based thereupon, a charge distribution on the photodetector can be determined, which then forms the basis for determining where the gamma quantum impacted and where it was emitted. Thereby, the collimator 21 allows capturing only gamma quanta 25 originating from the process in the subject 23 to be imaged. The detection of other (random) gamma quanta originating from other sources than the process in the subject to be imaged is prevented. The use of a collimator 21 is particularly important in SPECT imaging where single gamma quanta are detected and where external radiation has to be filtered out based on its angle of incidence. In PET imaging, there is usually not required a collimator as coincidence detection is used for filtering the incident gamma quanta.

Figure 5:
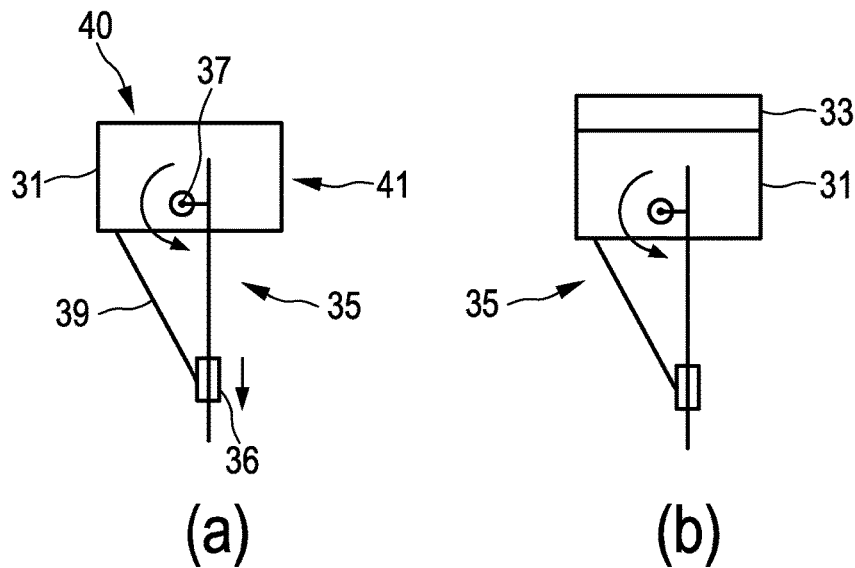
FIG. 5 shows a schematic illustration of a positioning mechanism according to an embodiment of the present invention.

Detecting high energy gamma quanta (PET imaging) usually requires thicker scintillator elements than detecting low energy gamma quanta (SPECT imaging). In a first embodiment of the present invention, as illustrated in FIG. 5, switching between the two operation modes is thus realized by means of a positioning mechanism 35. A scintillator element 31, as illustrated in FIG. 5(a), or a scintillator element 31 with a thereto attached photosensitive element 33, as illustrated in FIG. 5(b), is tilted, i.e. rotated (preferably by an angle of 90°), by means of a positioning mechanism 35. In the illustrated example, the positioning mechanism 35 basically relies on a single point of attachment 37 in which the scintillator element 31 or the scintillator element 31 and the thereto attached photosensitive element 33 is pivotably supported. By moving the sliding element 36 along the indicated direction, the element can be rotated. There is further illustrated a support structure 39 for supporting or fixating the scintillator element 31 in one of two possible positions. This support structure 39 works together with the sliding element 36 to tilt the element. The first position (first operation mode of the apparatus) thereby comprises the scintillator element 31 oriented versus the subject with a first side 40, the second position (second operation mode of the apparatus), after turning the scintillator element 31, comprises the scintillator element 31 oriented versus a subject with its second side 41. Depending on which side (40, 41) of the scintillator element 31 is oriented versus the subject, incident gamma quanta impact on the scintillator element 31 from one side or the other. If the scintillator element 31 is then designed (e.g. in the form of a cuboid) to provide different edge lengths (as illustrated in FIG. 5), this has the effect, that incident gamma quanta have a longer (or shorter) distance for interacting with the scintillator element 31 (scintillator crystal) and for being absorbed depending on how the scintillator element 31 is oriented. A longer distance, i.e. a thicker scintillator, thereby allows capturing gamma quanta with higher energy that are more relevant to PET imaging while a thinner scintillator (i.e. a shorter distance) is better suited for the lower energy regime of SPECT imaging. The photosensitive element 33 allows capturing scintillation photons independent of the orientation of the scintillator element 31.

Figure 6:
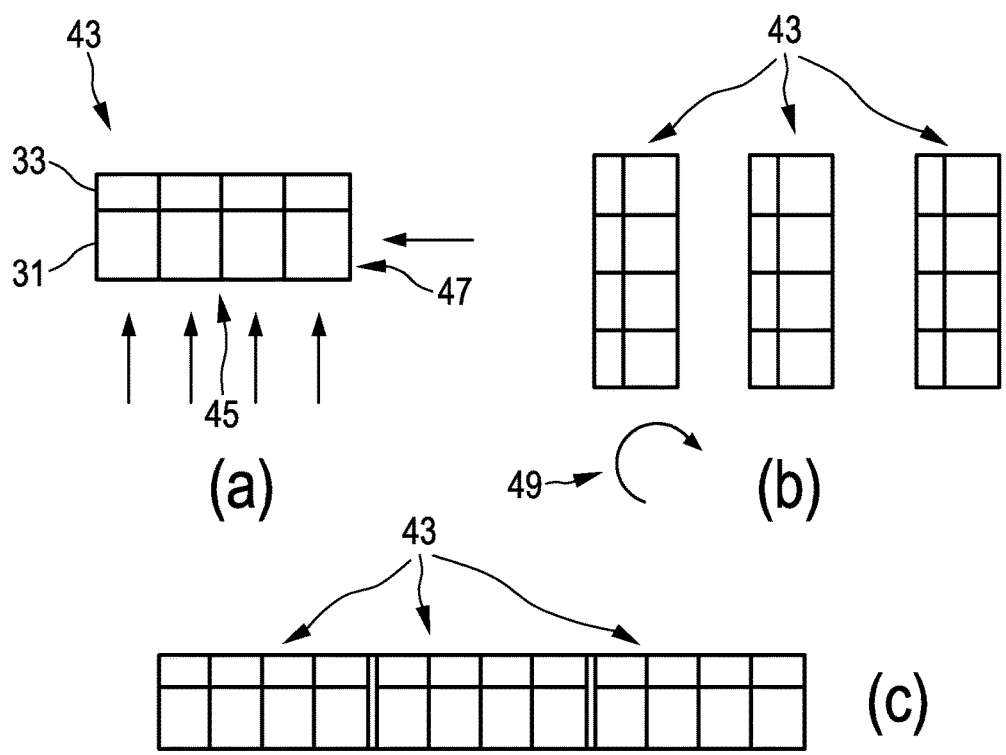
FIG. 6 shows a schematic illustration of the effect of tilting a detector module.

As illustrated in FIG. 6 it is also possible to tilt an entire detection assembly 43 comprising a plurality of scintillator elements 31 and thereto attached photosensitive elements 33. FIG. 6(*a*) illustrates a detection assembly 43 comprising a stack of scintillator elements 31. By means of tilting said detection assembly 43 it becomes possible to orient either a first side 45 (side face of the stack) or a second side 47 (top face of the stack) versus the subject and the therefrom originating gamma quanta. Depending on which of the first side 45 and the second side 47 is oriented versus the subject, the gamma quanta emitted by the process in the subject may impact on the first side 45 or on the second side 47 of the stack of scintillator elements 31 as indicated in FIG. 6(*a*). If the gamma quanta impact on the second side 47 they may be absorbed in four scintillator elements 31 as they may pass from one scintillator element 31 to the next. There is thus provided a comparably long distance for a possible interaction (absorption) of incident gamma quanta with the scintillator. The apparatus is thus in a second operation mode particularly suited for the detection of high energy gamma quanta (which may pass through a thinner scintillator crystal with only a low probability of absorption). If the scintillator elements 31 are tilted and the gamma quanta enter the scintillator elements 31 from the first side 45 after the detection assembly has been tilted, the distance for a possible absorption and generation of scintillation photons is shorter. This makes the stack of scintillator elements particularly suited for the detection of low energy gamma quanta (first operation mode).

FIG. 6(*b*) illustrates three detection assemblies 43 and a direction of a rotation 49. FIG. 6(*c*) illustrates the three detection assemblies after being tilted (rotated by an angle of 90°) as indicated in FIG. 6(*b*). As illustrated in FIGS. 6(*b*) and (*c*) the area covered by the scintillator is usually larger if low energy gamma quanta are to be detected (first operation mode).

The rotation (tilting) of the scintillator elements 31 or detection assemblies 43 is usually done in a synchronous way for all elements or assemblies. The movement may be induced by a motor or, preferably, by air pressure cylinders to allow a fast switching between the two positions (and operation modes). Many other mechanical options are possible. It may also be possible to use a guide rail or comparable mechanical structure for moving the scintillator elements or detection assemblies from a first position with a first side directed to the subject to a second position with a second side directed to the subject.

Figure 7:
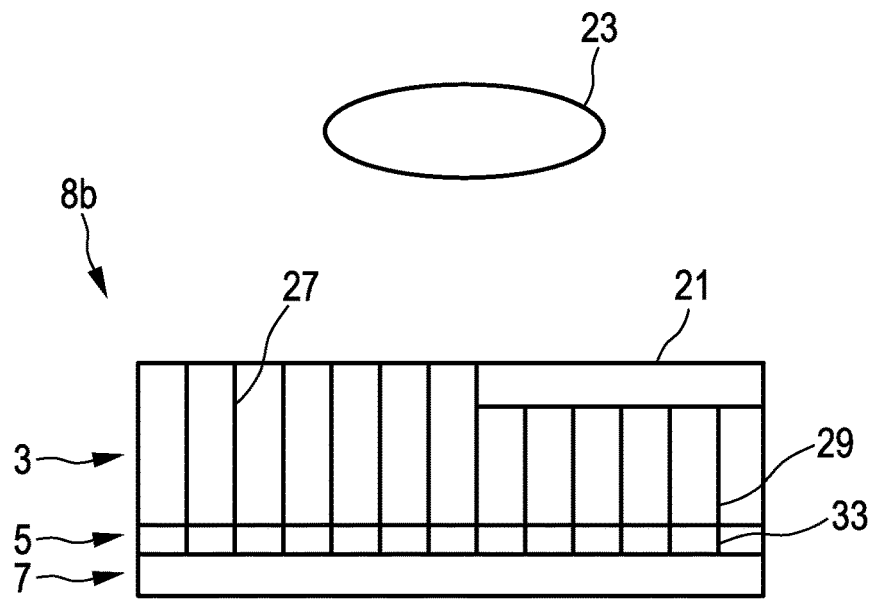
FIG. 7 illustrates schematically (in sectional view) a hybrid scintillator array comprising low energy scintillator elements and high energy scintillator elements according to another embodiment of the present invention.

In another embodiment of the present invention, the switching between the two operation modes according to the present invention is achieved by combining differently dimensioned scintillator elements in one detector module. FIG. 7 illustrates a sectional view of a detection module 8*b* in an apparatus according to another embodiment of the present invention. Said module 8*b* comprises two different types of scintillator elements, i.e. high energy scintillator elements 27 (usually longer crystals or maybe also including a different type of crystal) for capturing high energy gamma quanta (PET imaging) and low energy scintillator elements 29 for capturing low energy gamma quanta (SPECT imaging). A scintillator array 3 comprising different types of scintillator elements may also be referred to as hybrid scintillator array. The collimator 21 is arranged between the region with the low energy scintillator elements 29 and the subject 23 (as outlined above there is usually not needed a collimator in PET imaging). There is further illustrated a photodetector 5 including photosensitive elements 33 for capturing the scintillation photons emitted by the different scintillator elements 27, 29 in response to incident gamma quanta. Although not illustrated in FIG. 7 there may optionally also be comprised a light-guide between the scintillator 3 and the photodetector 5.

Figure 8:
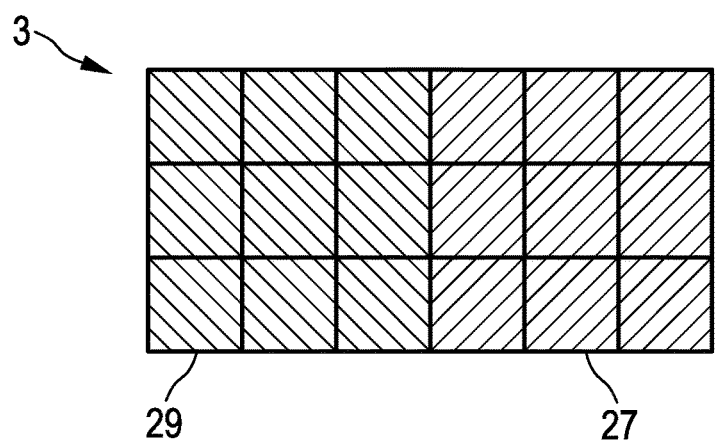
FIG. 8 illustrates a hybrid scintillator array in top view.

In FIG. 8 there is illustrated a top view of a possible arrangement of a scintillator 3 or hybrid scintillator array. The scintillator 3 comprises a region of high energy scintillator elements 27 and a region of low energy scintillator elements 29. Other embodiments may comprise other arrangements of the two regions comprising the different scintillator elements (e.g. alternating high energy and low energy scintillator elements or an annular array of high energy scintillator elements positioned axially adjacent to an annular array low energy scintillator elements). The hybrid scintillator array illustrated in FIG. 8 allows an apparatus for imaging as disclosed herein to be switched between the first operation mode and the second operation mode. The switching may, e.g. comprise configuring the readout electronics to discriminate and read out the low energy scintillator elements in the first operation mode and to read out the high energy scintillator elements in the second operation mode.

Figure 9:
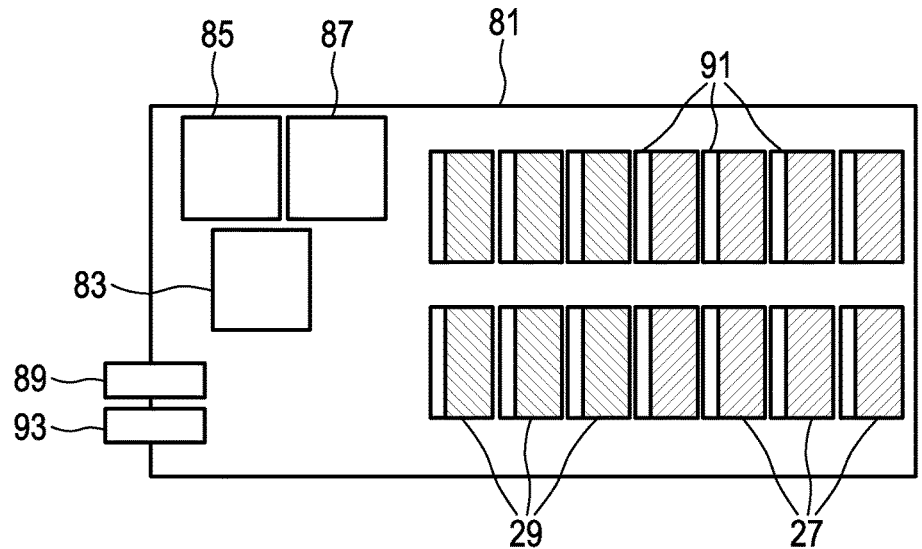
FIG. 9 shows a schematic illustration of the electronics data path at the frontend level compatible with both PET and SPECT operation and a possible partition in the combined frontend electronics between SPECT and PET scintillator elements.

An element of this embodiment is thereby that a detector module houses a hybrid frontend electronics capable of supporting distinct scintillator elements (and thereto coupled photosensitive elements), either optimized for PET or SPECT imaging. In FIG. 9 such a hybrid frontend electronics is schematically illustrated. A printed circuit board 81 made of FR4 or other suitable material like PTFE is equipped on the back side with a digital configurable processor 83 such as an FPGA or another type of reconfigurable embedded processor. Auxiliary electronic components relevant to high-performance information processing 85, 87, e.g. a DSP, a configurable coprocessor or a RAM module, may also be included. The frontend electronics can be considered to be part of the readout electronics. Information is transmitted from the frontend electronics to other parts of the readout electronics (in particular a central processing unit for image reconstruction) by means of an interface 89. The interface 89 may, e.g., be implemented in form of a wired, wireless or optical connection using either serial or parallel encoded bit streams. Multi-pin connections 91, realized as either in physical multi-row connectors or elastomeric connectors can be used to assure connection to high energy or low energy scintillator elements and thereto coupled photosensitive elements.

FIG. 9 illustrates a possible configuration with a group of 4×2 high energy (PET) scintillator elements 27 (and thereto coupled photosensitive elements) and a group of 3×2 low energy (SPECT) scintillator array elements 29 (and thereto coupled photosensitive elements). Obviously, other configurations are possible depending on the layout of the PCB board 81 and on the desired imaging modalities. It may also be possible that different types of photosensitive elements are used for different scintillator elements (more appropriate for PET or SPECT). Besides the interface 89 to the central processing unit, the frontend electronics further includes a power connection 93 that may be implemented in form of a parallel connection or in form of a single hybrid cable.

Figure 10:
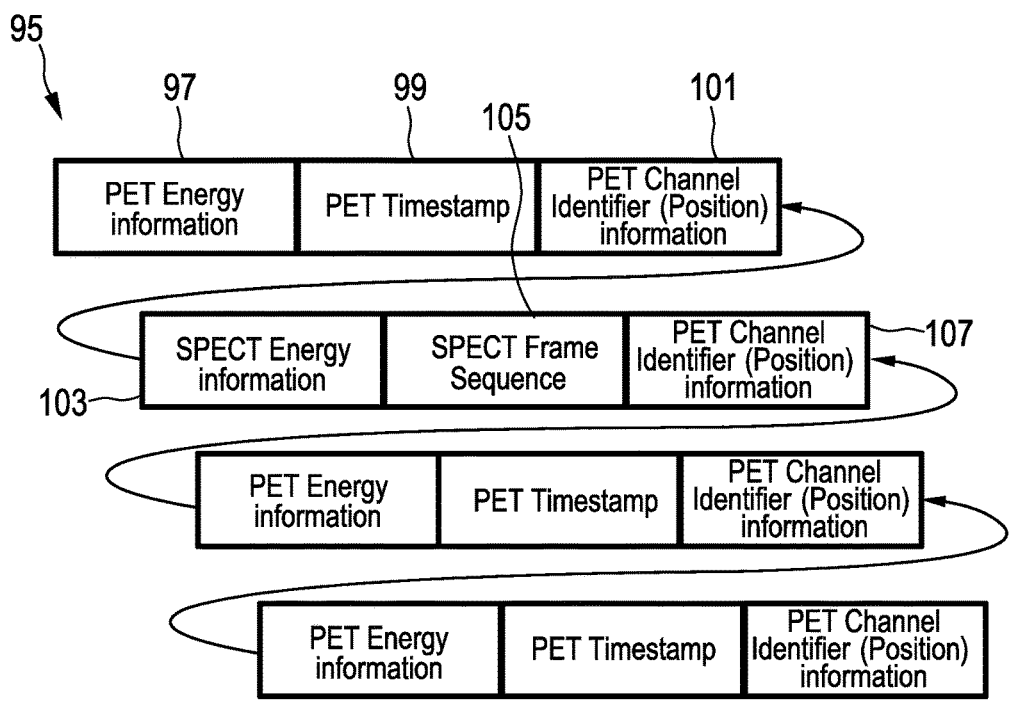
FIG. 10 illustrates schematically a typical combined PET/SPECT data packet.

In FIG. 10, a possible data packet 95 that may be transmitted over the interface 89 is illustrated. For processing data arising from photosensitive elements coupled to the high energy scintillator elements 27 (second operation mode, i.e. PET operation mode), the frontend processor 83 will compute the energy 97 of two detected PET gamma quanta, a timestamp 99 with a precision of the order of tenths of picoseconds to allow for Time-of-Flight (TOF) imaging as well as a channel identifier 101 that locates the three dimensional spatial position of the interaction of the two PET gamma quanta. For processing data arising from photosensitive elements coupled to low energy scintillator elements (first operation mode, i.e. SPECT operation mode), the energy field 103 contains information of only one gamma quanta. Mode information of timing of a photon is not used and the timestamp information is replaced by a nanosecond frame sequence 105. The corresponding spatial information decoded from the SPECT information is placed in field 107. Data arising from PET and SPECT scintillator elements are grouped by the frontend processor in a combined package 95 and sent via the data link to a central processor.

FIG. 10 shows an exemplary combined package 95 comprising three PET events interleaved with one SPECT event. The filtering can be implemented either by hardware or by software. In a possible implementation, multiple data links are concentrated in a central processing unit that discriminates information from PET and SPECT scintillator elements based on the payload field 101, 107 and sends the data to different computers, processors or GPUs for the final image reconstruction. Usually, qualified PET coincidence data as well as SPECT data is transferred to a computer and stored in a mass storage element for image reconstruction.

Figure 11:
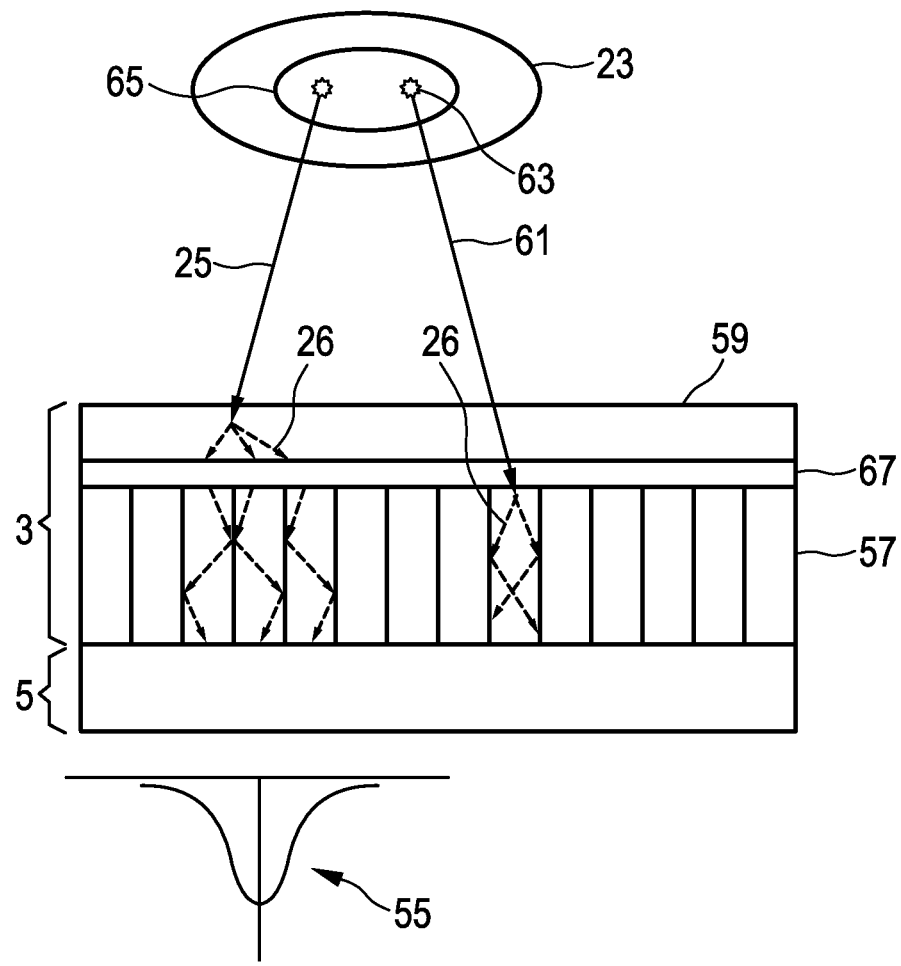
FIG. 11 illustrates schematically (in sectional view) a detection module for allowing switching a multimodal imaging apparatus between two operation modes according to another embodiment of the present invention.

FIG. 11 illustrates yet another embodiment of the present invention for allowing switching a multimodal imaging apparatus between two operation modes. Thereby the scintillator 3 comprises high energy scintillator elements 57 as well as low energy scintillator elements 59. The low energy scintillator elements 59 are arranged between the subject 23 and the high energy scintillator elements 57. Further, there is included an optical coupling 67 (e.g. light-conductive glue) between the high energy scintillator elements 57 and the low energy scintillator elements 59. A process 63 in subject 23 may either cause the emission of low energy gamma quanta 25 (SPECT imaging) or high energy gamma quanta 61 (PET imaging) in an area of interest 65 within the subject 23. If the process 63 causes the emission of a low energy gamma quantum 25 this low energy gamma quantum 25 causes the emission of scintillation photons 26 in the low energy scintillator elements 59. If the process 63 causes the emission of a high energy gamma quantum 61 this high energy gamma quantum 61 usually has too much energy for being absorbed and for causing the emission of scintillation photons 26 in the low energy scintillator 59. The gamma quantum 61 can then pass through the low energy scintillator 59 without being absorbed and cause the emission of scintillation photons 26 in the high energy scintillator elements 57. Scintillation photons 26 emitted in the low energy scintillator elements 59 may pass through the high energy scintillator elements 57. All scintillation photons 26 are captured by the photodetector 5. Thereby, the photodetector 5 can be coupled to the scintillator 3 in light sharing configuration or in individual one-to-one coupling and a charge-distribution 55 of the scintillation photons on the photodetector 5 can be determined.

Figure 12:
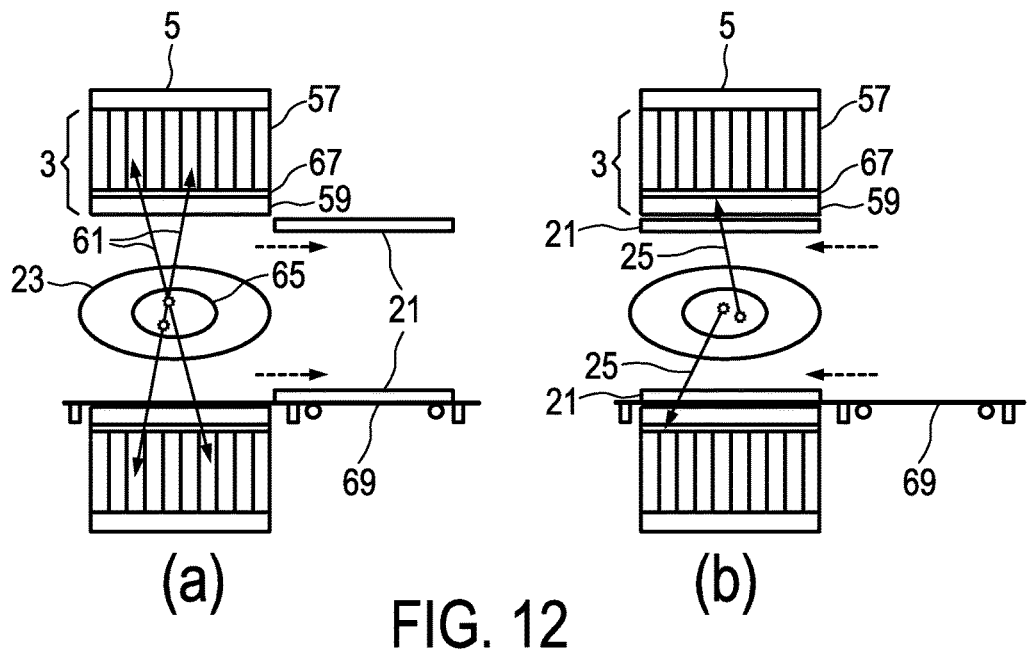
FIG. 12 illustrates schematically the effect of using shifting means for shifting the collimator between the SPECT and the PET acquisition positions.

However, it is usually necessary to filter the low energy gamma quanta (SPECT imaging) in order to prevent the detection of photons not originating from the desired area of interest. Therefore, usually a collimator is used. This is usually not necessary if coincidence detection (i.e. a simultaneous impacts of the two high energy gamma quanta usually defined as a time difference of both impacts being within a programmable time window) is used in case of high energy gamma quanta (PET imaging). Thus, this embodiment of the present invention requires a collimator between the subject and the scintillator in the first operation mode and no collimator in the second operation mode. There is illustrated in FIG. 12(*a*) a PET process causing the emission of two high energy gamma quanta in opposite directions and on the right side a SPECT process causing the emission of single photons. In the illustrated embodiment of the present invention, shifting means 69 are used for shifting the collimator 21 in a first position in the direct path between the scintillator 3 and the subject 23 (FIG. 12(*b*)), or in a second position outside of the direct path between the scintillator 3 and the subject 23 (FIG. 12(*a*)). Thus, it is possible that incident gamma quanta pass the collimator (FIG. 12(*b*)) or not (FIG. 12(*a*)). For PET imaging (high energy gamma quanta, second operation mode of the apparatus), the collimator 21 is out of the direct path between the area of interest in the subject and the detector module as illustrated (FIG. 12(*a*)). For SPECT imaging (low energy gamma quanta, first operation mode of the apparatus) the collimator 21 is in the direct path (FIG. 12(*b*)). The shifting structure 69 may thereby particularly be represented by a guide rail structure or the like and allow the collimator 21 to slide in and out of the direct path.

Figure 13:
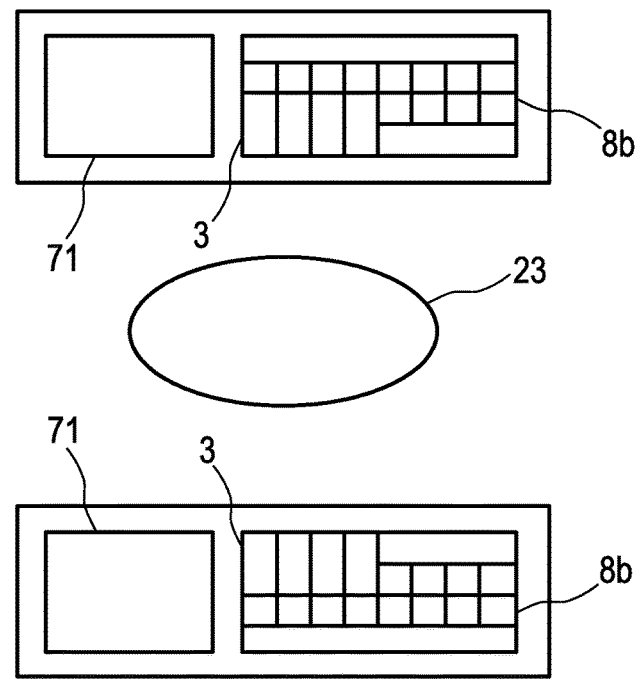
FIG. 13 illustrates schematically a hybrid CT/PET/SPECT system with a common gantry PET/SPECT system according to an embodiment of the present invention.
Figure 14:
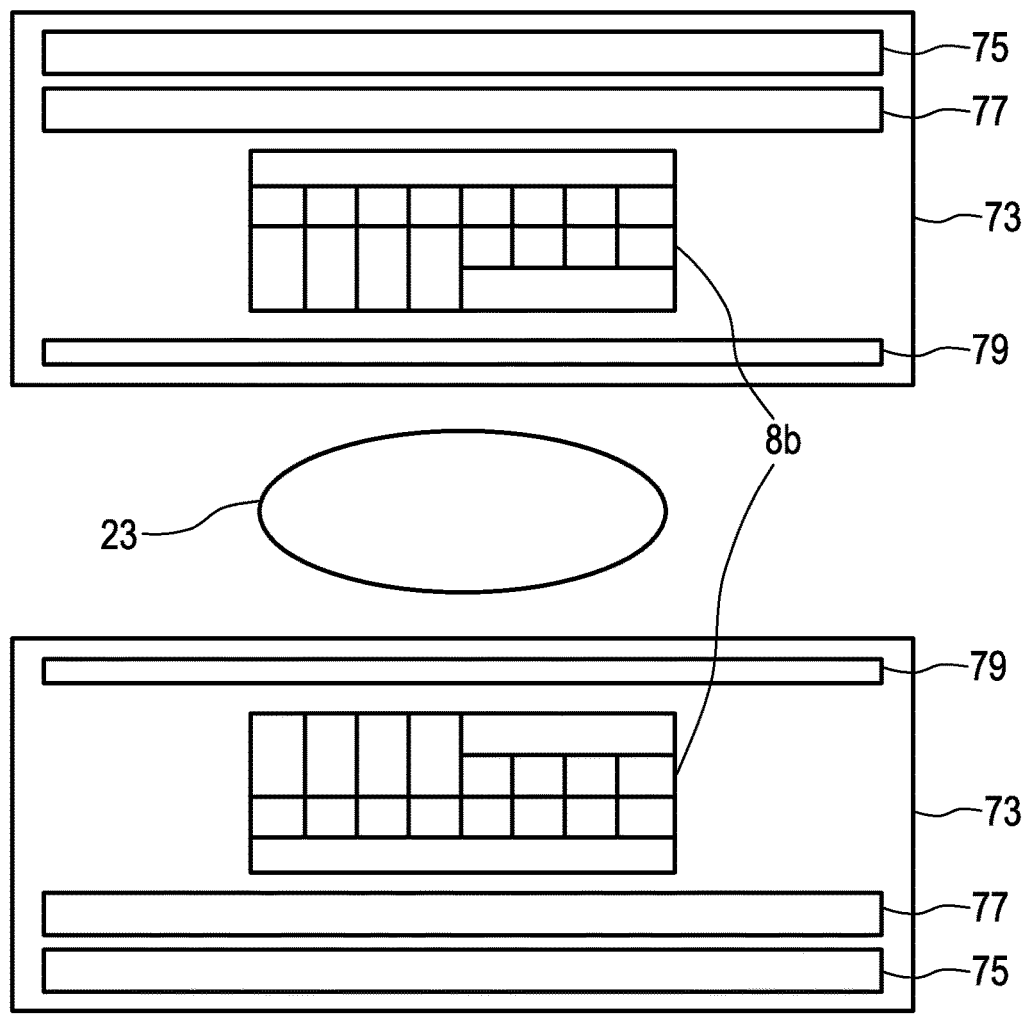
FIG. 14 illustrates schematically a possible embodiment of a hybrid MRI/PET/SPECT system with a common gantry PET/SPECT system according to an embodiment of the present invention.
Figure 15:
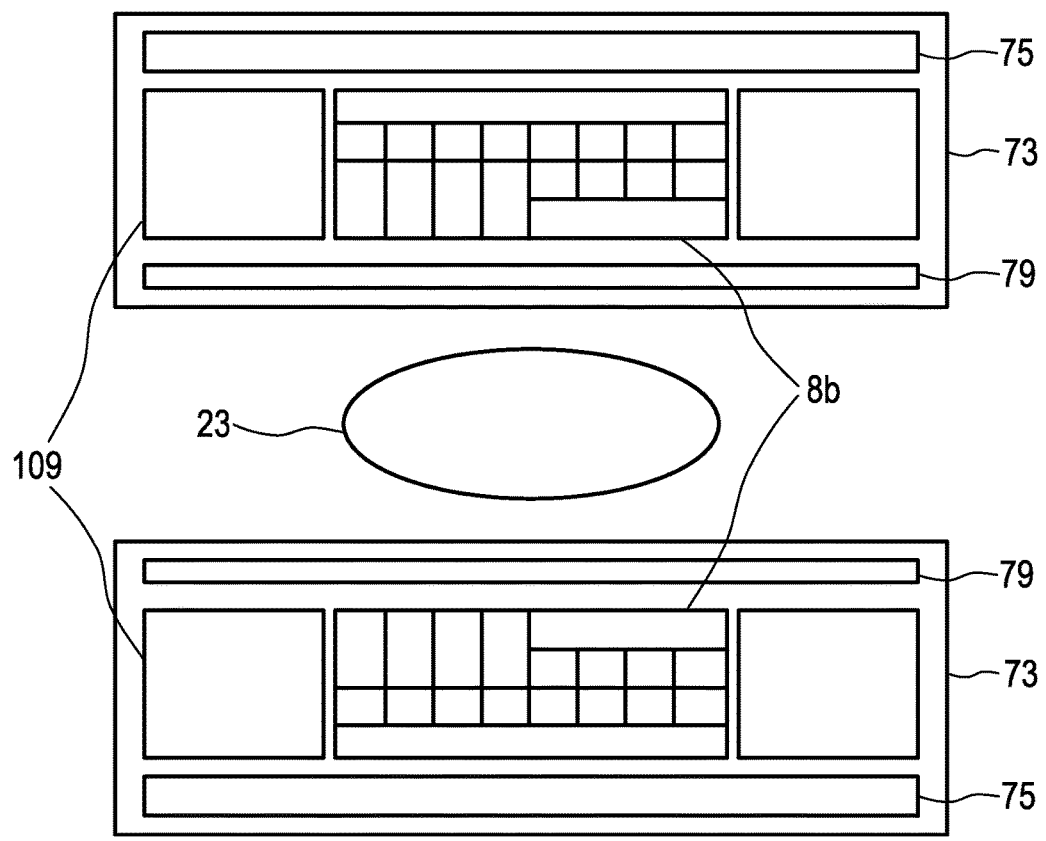
FIG. 15 illustrates schematically another possible embodiment of a hybrid MRI/PET/SPECT system with a common gantry PET/SPECT system according to an embodiment of the present invention.

FIGS. 13 to 15 are schematic illustrations (in sectional view) of combined imaging apparatus that are based on a multimodal imaging (PET and SPECT images substantially from the same area of interest) apparatus as disclosed above and that include further imaging modalities (CT or MRI). Thereby again, the same common gantry is used. FIGS. 13 to 15 thereby show detection modules 8*b* that are based on differently dimensioned scintillator elements (as further detailed in FIGS. 7 to 9). Switching between a first operation mode and a second operation mode is thus achieved by reading out the high energy scintillator elements or the low energy scintillator elements, respectively. It may, however, also be possible to make use of the other illustrated switching approaches by means of a positioning mechanism (FIGS. 5 and 6) or by shifting means (FIG. 12) analogously. FIGS. 13 to 15 further illustrate a subject 23 situated in an examination area inside of a gantry to which the detection modules are attached to. The detection modules are placed at a given distance from the center of the field of view (examination area) compatible with a CT or MRI system.

In FIG. 13 there is illustrated an imaging apparatus allowing to image a process in a subject based on PET and SPECT imaging. There is further comprised an abutted (or integrated) CT imaging modality 71 for generating computed tomography images of the subject 23 within the same system housing 73.

FIG. 14 illustrates a combination of the detection module 8b with a magnetic resonance imaging (MRI) modality within the same system housing 73. Such a combined PET/SPECT/MRI system usually comprises a magnet 75, a gradient coil 77 and a radiofrequency (RF) coil 79. Due to the strong static and alternating magnetic fields of the MRI system the collimator then usually needs to be constructed from a suitable material like tungsten.

According to yet another embodiment of the present invention, as illustrated in FIG. 15, it is also possible to combine the detection module 8b with a split-gradient MRI imaging system. In this combined system split-gradients 109 are used and the detection module 8b is placed within the split-gradient. This configuration allows reducing the space between the gradient and the RF coil, thereby allowing building a PET/SPECT/MRI system with a larger system bore.

In the illustrated embodiments of the present invention, the photosensitive elements comprised in the photodetector may particularly be incorporated by a digital SiPM like the PHILIPS Digital Photon Counter capable of performing single photon counting or equivalent analog devices like photomultipliers (PMT) or SiPMs that are read out by a mixed signal application-specific integrated circuit (ASIC) that performs signal amplification and energy/time extraction either by counting, sampling or multiple thresholds. The digital information from the photosensitive elements is usually sent to a concentrator FPGA that filters the data, packs and transmits the collected events (PET or SPECT events) over a copper or optical fiber communication interface. As disclosed herein the data processing equipment is usually referred to as read out electronics or forms part of the readout electronics.

The photodetector and the scintillator may be coupled in one-to-one coupling, wherein each scintillator element is separately read out by a dedicated photosensitive element. Alternatively it may also be possible to make use of the light-sharing method, wherein multiple photosensitive elements capture the scintillation photons of the same scintillator element (and one photosensitive element captures the scintillation photons of different scintillator elements). This light-sharing method allows reducing the number of photosensitive elements which may result in reduced costs of the device.

The collimator may usually be represented by a block of lead, molybdenum, tungsten, depleted uranium or other suitable high-Z material, and include a plurality of aligned boreholes. A suitable collimator for low energy photon selection (e.g. <250 keV) is usually used.

The apparatus disclosed herein can be used either for PET or SPECT, or simultaneous PET and SPECT imaging. Step-wise or continuous subject motion in axial direction in order to obtain a full body patient exam are both possible. The modular concept allows a comfortable and flexible product customization and upgrade strategy.

According to an other embodiment similar to the illustration in FIG. 6, a 20 mm long crystal (LYSO, LSO, Garnet, BGO or other scintillator material) may be subdivided into four pixels (scintillator elements) of 5 mm length each. Photosensitive elements (SiPM, APD, photodiodes) may be optically coupled to the scintillator elements along a 20 mm long side. The face of the crystal used for PET detection may then have a size of 4×4 mm$^2$, the four faces of the sub-crystals used for SPECT have 5×4 mm$^2$ size. Therefore the detector area for SPECT imaging is five times larger than for PET, enabling high efficiency SPECT. Modification of these numbers in other embodiments is of course possible.

Possible scintillator materials may include crystal arrays or blocks made of LYSO:Ce, LSO:Ce, LuAP:Ce, LuYAG:Ce, BGO, ceramic garnets or another heavy inorganic scintillator. PET scintillator array elements may typically require some 2 cm of high density scintillator material while SPECT scintillator array elements may typically require some 2 cm of low density scintillator material. The scintillator elements are usually either optimized for PET or for SPECT. Scintillator elements optimized for PET may either use pixelated crystals, typically a heavy high-Z inorganic scintillator crystal (LYSO, LSO, GSO, BGO or ceramic garnets) with cross-sections adequate either for clinical (2 to 4 mm) or preclinical (about 1 mm) applications. Typical lengths are usually around 12 to 25 mm (clinical) and 8-12 mm (preclinical applications). Scintillator elements optimized for SPECT may use the same type of photosensitive elements or may use other types depending on the required performance. As material for shorter scintillator crystals (typically around 5 mm) there are usually used ceramic garnets optimized for high light yield, such as CsI:Tl or NaLTl. In front of the SPECT region there is usually placed a suitable collimator 21 to perform an angular selection of the incoming gamma quanta.

Switching between the two operation modes may be implemented in soft- or hardware. Embodiments of the present invention my, e.g. also allow a kind of pay per view mode in dual-mode-prepared imaging apparatus. Different quality levels of apparatus may be offered depending on the used scintillator crystals.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A multimodal imaging apparatus for imaging a radiotracer distribution within a subject, said apparatus comprising:
   at least two detector assemblies, each detector assembly including an array of subassemblies, each subassembly including:
      a scintillator including scintillator elements configured to capture incident gamma quanta generated by the radiotracer and emit scintillation photons in response to said captured gamma quanta;

a photodetector including photosensitive elements configured to capture the emitted scintillation photons and determine a spatial distribution of the scintillation photons;

a readout electronics configured to determine an impact position of an incident gamma quantum in the scintillator and/or a parameter indicative of an emission point of the gamma quantum in the subject based on a spatial distribution of the scintillation photons;

a positioning mechanism configured to tilt each subassembly individually to switch the imaging apparatus between a first operational mode for detecting low energy gamma quanta and a second operational mode for detecting high energy gamma quanta, wherein the high energy gamma quanta have a higher energy than the low energy gamma quanta; and wherein the scintillator of each subassembly is arranged to capture incident gamma quanta from the same area of interest in the first operational mode and in the second operational mode.

2. The multimodal imaging apparatus according to claim 1, wherein the energy of both the low energy gamma quanta and the high energy gamma quanta lies between 70 keV and 600 keV.

3. The multimodal imaging apparatus according to claim 1 further comprising a common gantry for supporting the subassemblies in the first operational mode and in the second operational mode.

4. The multimodal imaging apparatus according to claim 1, further comprising a collimator configured to filter the incident gamma quanta based on an angle of incidence in the first operational mode.

5. The multimodal imaging apparatus according to claim 1, wherein
the photodetector is configured for operation in photon counting mode, wherein the dynamic range of the photodetector is configured to capture scintillation photons emitted by both the high energy scintillator elements and by the low energy scintillator elements.

6. The multimodal imaging apparatus according to claim 1, wherein
one photosensitive element is coupled to each scintillator element and arranged to capture the scintillation photons emitted by said scintillator element; and
the positioning mechanism is configured to tilt the scintillator elements and the thereto coupled photosensitive elements such that the gamma photons travel along a shorter dimension in the first operational mode and the along a longer dimension in the second operational mode.

7. The multimodal imaging apparatus according to claim 1, wherein each detector assembly includes an M×N array of subassemblies, where M and N are plural integers.

8. The multimodal imaging apparatus according to claim 1, wherein
each subassembly includes a stack of scintillator elements; and
the positioning mechanism is configured to tilt said stack of scintillator elements for switching the imaging apparatus between a first position corresponding to the first operational mode in which the incident gamma quanta impact on the side face of the stack and a second position corresponding to the second operational mode in which the incident gamma quanta impact on the top face of the stack.

9. The multimodal imaging apparatus according to claim 7, wherein each subassembly has a single scintillation element optically coupled to a single photodetector element such that each detector has M×N subassemblies to provide the same resolution and field of view in both the first and second operational modes.

10. The multimodal imaging apparatus according to claim 1, wherein the readout electronics are configured to read out low energy gamma quantum events in the first operational mode and to read out high energy gamma quantum events in the second operational mode.

11. The multimodal imaging apparatus according to claim 1, wherein the scintillator comprises an array of scintillator elements including a first region corresponding to a two-dimensional area of the array facing an area of interest in the first operation mode with low energy scintillator elements configured to capture low energy gamma quanta and a second region corresponding to a two-dimensional area of the array facing the area of interest in the second operation mode with high energy scintillator elements configured to capture high energy gamma quanta.

12. A multimodal imaging apparatus for imaging a radiotracer distribution within a subject, said apparatus comprising:
a plurality of detector assemblies, each detector assembly including a two-dimensional array of subassemblies, each subassembly including:
at least one scintillator element configured to capture incident gamma quanta generated by the radiotracer and emit scintillation photons in response to said captured gamma quanta,
at least one photosensitive element configured to capture the emitted scintillation photons, each photosensitive element being optically coupled to a first face of a corresponding scintillator element; and
a mechanical positioning mechanism configured to rotate each subassembly relative to the corresponding detector assembly between a first orientation in which the incident gamma photons are received on a second face of the scintillation elements, the second face being disposed opposite to the first face and a second orientation orthogonal to the first orientation such that the incident gamma photons are received on a side face of one of the scintillation elements.

13. The multimodal imaging apparatus according to claim 12, wherein each subassembly includes a single scintillator element and a single detector element such that each detector assembly has the same number of scintillator element/photosensitive element pairs in both of the orientations.

14. The multimodal imaging apparatus according to claim 13, further including:
readout electronics configured to determine the capture location of incident gamma quantum in the scintillator and/or a parameter indicative of an emission point of the gamma quantum in the subject based on a spatial distribution of the scintillation photons.

15. The multimodal imaging apparatus according to claim 12, wherein each subassembly includes a liner array of scintillator elements optically coupled to a linear array of photodetectors such that in the second orientation incident gamma photons pass serially through adjacent scintillator elements of each subassembly from side face to side face.

16. The multimodal imaging apparatus according to claim 12, wherein the two-dimensional array includes M×N subassemblies, where M and N are plural integers.

17. A multimodal imaging apparatus for imaging a radiotracer distribution within a subject, the apparatus comprising:

a plurality of radiation detector modules, each detector module including:
- a plurality of first scintillator elements configured to capture lower energy incident gamma radiation quanta generated by the radiotracer and to emit scintillation photons in response to the captured lower energy gamma quanta,
- a plurality of second scintillator elements configured to capture higher energy incident gamma radiation quanta generated by the radiotracer and to emit scintillation photons in response to the captured higher energy gamma quanta,
- a plurality of photosensitive elements optically coupled to the first and second scintillator elements and configured to capture the emitted scintillation photons,
- a collimator system including collimator elements disposed on a face of the first scintillator elements and configured to filter the incident gamma quanta based on an angle of incidence, the collimator elements being disposed between the first scintillator elements and the subject, and the collimator system including no collimator elements between the second scintillator elements and the subject.

18. The multimodal imaging apparatus according to claim 17, further including:
readout electronics configured to determine the capture location of incident gamma quantum in the scintillator elements and/or a parameter indicative of an emission point of the gamma quantum in the subject based on a spatial distribution of the scintillation photons.

* * * * *